United States Patent [19]

Marshall

[11] Patent Number: 5,601,848
[45] Date of Patent: Feb. 11, 1997

[54] METHODS FOR THE TREATMENT OF GASTROINTESTINAL DISORDERS

[75] Inventor: Barry J. Marshall, Perth, Australia

[73] Assignee: The Procter & Gamble Company, Cincinnati, Ohio

[21] Appl. No.: 70,857

[22] Filed: Jul. 8, 1987

Related U.S. Application Data

[63] Continuation of Ser. No. 744,842, Jun. 13, 1985, abandoned.

[51] Int. Cl.$^6$ .................... A61K 33/24; A61K 31/60; A61K 31/29
[52] U.S. Cl. .................... 424/653; 514/159; 514/503
[58] Field of Search .................... 424/131, 653; 514/159, 503

[56] References Cited

U.S. PATENT DOCUMENTS

| | | | |
|---|---|---|---|
| 3,247,051 | 4/1966 | Leebrick | 167/22 |
| 3,577,533 | 5/1971 | Rider | 424/155 |
| 4,016,268 | 4/1977 | Goldenberg et al. | 424/231 |
| 4,118,480 | 10/1978 | Williams | 424/131 |
| 4,153,685 | 5/1979 | Serfontein | 424/94 |

FOREIGN PATENT DOCUMENTS

| | | |
|---|---|---|
| 2014/61 | 3/1963 | Australia . |
| 65846/65 | 5/1967 | Australia . |
| 0075992 | 4/1983 | European Pat. Off. . |
| 5877 | 3/1968 | France . |
| 5877M | 4/1968 | France . |
| 6197 | 7/1968 | France . |
| 6531 | 12/1968 | France . |
| 1963496 | 6/1971 | Germany . |
| 1107655 | 3/1968 | United Kingdom . |
| 1478742 | 7/1977 | United Kingdom . |

OTHER PUBLICATIONS

Drugs 12:401–411 (Brogden et al) 1984.
The Lancet, Jun. 4, 1983, pp. 1273–1275.
*Gastroenterology,* 78(6):1495–1499 (Jun.) 1980.
Gastroenterology 82(5):864–70, May 1982.
*The Medical Journal of Australia,* vol. 142 Apr. 15, 1985 Marshall et al.
*The New England Journal of Medicine,* Dec. 10, 1981 pp. 1444–1452 Blaser.
*The Lancet,* Sep. 1, 1984, 525–526.
The Lancet, 16 Jun. 1984, pp. 1311–1315.
*The Lancet,* Aug. 4, 1984, p. 281; May 12, 1984 (McNulty).
Jour. DD. Oct. 1940 vol. VII No. 10 443–445.
The Lancet, Jun. 16, 1984, pp. 1348–1349 & 1336–1337.
Annales Pharmaceutiques Francaises, vol. 38, No. 5, pp. 447–454 (1980).
Chemical Abstracts Service (Columbus, Ohio) abstract, vol. 98, p. 15, No. 172475y (1983).
Chemical Abstracts Service (Columbus, Ohio) abstract, vol. 98, p. 384, No. 221850c (1983).
Steer, "Surface morphology of the gastroduodenal mucosa in duodenal ulceration", *Gut,* 25, pp. 1203–1210 (1984).

Marshall and Warren, "Spiral bacteria in the human stomach: a common finding in patients with gastritis and duodenal ulcer" in: Campylobacter II, Proceedings of the Second International Workshop on Campylobacter Infections (London, 1983; Public Health Laboratory Service; Pearson, Skirrow et al., editors), pp. 11–12.
Abstract: "Histological Improvement of Active Chronic Gastritis in Patients Treated with De–Nol", presented at a meeting of the Gastroenterological Society of Australia, Mar. 11–14, 1984, Melbourne, Australia.
M. B. Skirrow, "Report on the Session" in Campylobacter II, Proceedings of the Second International Workshop on Campylobacter Infections (London, 1983; Public Health Laboratory Service; Pearson, Skirrow et al., editors), pp. 5–10.
"Bismosal, Mixture Cholera Infantum, Norwich" (Advertisement) (1918).
"Stomach Upset" (Advertisement) (1951).
B. J. Marshall, I. Hislop et al, "Histological Improvement of Active Chronic Gastritis in Patients Treated with De–Nol", 14 Australia & New Zealand J. of Medicine 907 (Dec., 1984).
B. J. Marshall, "Perspective–Campylobacter pyloridis and Gastritis" 153 J. of Infectious Diseases 650–657 (1986).
S. Zhang, et al., "Protective Effects of Furazolidone and Some Commonly Used Antiulcer Drugs on Several Gastric Ulcer Models in Rats", 19 Yaoxue Xuebao 5–11 (1984).
Physicians Desk Reference for Nonprescription Drugs 646 (1985).
L. Lu, et al., "Effect of Furaxon and It Analogs on Gastrointestinal Propulsion in Mice", 15 Beijing Yixueyuan Xuebao 185–187 (1983).
B. E. He, et al., "Cytoprotection of Furazolidone in Resistant–Soakage Gastric Ulcers in Rats", 4 Jinau Liyi Xuebao 55–59 (1984).
K. I. Shirokova, et al., "The Use of Metronidazole in Treatment of Patients with Ulcerative Disease", 59 Klin. Med.—(Mosk) 48–50 (1981).
Z. T. Zheng, et al., "Treatment of Gastrointestinal Ulcer by Furazolidone", 2 Chinese J. of Digestion 131–133 (1982).
Z. Zheng, et al., "Bouble–blind Short–term Trial of Furazolidone in Peptic Ulcer" 1 *Lancet* 1048–1049 (1985).
C. McNulty, et al., "Rapid Diagnosis of Campylobacter–Associated Gastritis" 1 *Lancet* 1443–1444 (1985).
A. McLean, et al., "Microbes, Peptic Ulcer and Relapse Rates with Different Drugs", 2 *Lancet* 525–526 (1984).

(List continued on next page.)

*Primary Examiner*—Raymond Henley, III
*Attorney, Agent, or Firm*—Kim William Zerby; Mary Catherine Poland; Douglas C. Mohl

[57] ABSTRACT

Method for the treatment of human and lower animals having an infectious gastrointestinal disorder, comprising the step of administering from about 50 to about 5000 milligrams of bismuth to said subject, per day, for from 3 to 56 days. Preferred processes also include a step for performing a diagnostic step on the subject for detection of campylobacter-like organism infection of the subject.

22 Claims, No Drawings

OTHER PUBLICATIONS

B. Marshall, et al., "Pyloric Campylobacter Infection and Gastroduodenal Disease" 142 *Medical Journal of Australia* 439–444 (1985).

R. Burnett, et al., "Campylobacter–like Organisms in the Stomach of Patients and Healthy Individuals" 1 *Lancet* 1349 (1984).

B. Marshall, et al., "Pyloric Campylobacter Serology" 2 *Lancet* 281 (1984).

B. Marshall, et al., "Unidentified Curved Bacilli in the Stomach of Patients with Gastritis and Peptic Ulceration" 1 *Lancet* 1311–1315 (1984).

M. Langenberg, et al., "Campylobacter–like Organisms in the Stomach of Patients and Healthy Individuals" 1 *Lancet* 1348 (1984).

Z. Zheng, et al., "A Double–blind Short–term Clinical Trial of the Effect of Furazolidone in Peptic Ulcer", 23 *Chinese J. of Int. Medicine* 195–197 (1984).

C. McNulty, et al., "Spiral Bacteria of the Gastric Antrum" 1 *Lancet* 1068 (1984).

J. Warren, "Unidentified Curved Bacilli on Gastric Epithelium in Active Chronic Gastitis" 1 *Lancet* 1273 (1983).

B. Marshall, "Unidentified Curved Bacilli on Gastric Epithelium in Active Chronic Gastitis" 1 *Lancet* 1273–1275 (1983).

J. Koo, et al., "Selective Coating of Gastric Ulcer by Tripotassium Dicitrato Bismuthate in the Rat", 82 *Gastroenterology* 864–870 (1982).

M. Gregory, "The Effect of Tri–potassium Di–citrato Bismuthate on the Duodenal Mucosa During Ulceration" 62 *S.A. Medical Journal* 52–55 (1982).

M. Steinhoff, et al., "Bismuth Subsalicylate Therapy of Viral Gastroenteritis", 78 *Gastroenterology* 1495–1499 (1980).

M. Blaser, et al., "Campylobacter Enteritis", 305 *New England Journal of Medicine* 1444–1452 (1981).

A. Freedberg, et al., "The Presence of Spirochetes in Human Gastric Mucosa", 7 *American Journal of Digestive Diseases* 443–445 (1940).

M. Goldenberg, et al., "Protective Effects of Pepto–Bismol Liquid on the Gastric Mucosa of Rats", 69 *Gastroenterology* 636–640 (1975).

Colson, "The treatment of chronic colitis and colopathies by a new association of bismuth, mucilage, oxyquinoline and meprobamate", *Revue des corps de sante des Armees*, 7(2), pp. 319–334 (1966).

Gisselbrecht et al., "Treatment of constipation and colitis by the association of bismuth subnitrate and Karaya gum", Lyon Med., 223(18), pp. 951–958 (1970).

Navarranne, "Treatment of spasmodic and psychosomatic colopathies by a cicatrisant, antiseptic and anxiolytic medication combination", Therapie, XXII, pp. 419–426 (1967).

Heraud et al., "Therapeutic trial of an association of an insoluble bismuth salt and a Karaya gum in gastro–intestinal pathology", *Lille Medical*, 3rd Series vol. XIV, No. 6, supplement, pp. 677–679 (1969).

Chemical Abstracts Service (Columbus, Ohio) abstract, vol. 94, p. 93, No. 168025b (1981).

Unlisted Drugs, vol. 22, No. 11, p. 163b (Nov. 1970), "Aldefur".

Biological Abstracts, vol. 82, No. 1626, abstract No. 1623 (1986).

Unlisted Drugs, vol. 34, No. 3, p. 38; (Mar. 1982), "Corygest".

Rote List 1976, Editio Cantor, Aulendorf, Wurtt, DE; "Uplex 59051B".

METHODS FOR THE TREATMENT OF GASTROINTESTINAL DISORDERS

This is a continuation of application Ser. No. 744,842, filed on Jun. 13, 1985, now abandoned.

BACKGROUND OF THE INVENTION

This invention relates to methods for the treatment of infectious gastrointestinal disorders in humans and other animals.

Factors adversely affecting the function of the gastrointestinal system in humans are exceedingly varied in their nature. Such disorders may arise in the upper or lower gastrointestinal tracts or both. There is a broad range of causes of gastrointestinal disorders, including genetic, physiological, environmental, and psychogenic factors. Accordingly, the diagnosis and management of these disorders can be exceptionally difficult. A detailed discussion of gastrointestinal tract functions, disorders, causes, and treatments can be found in Spiro, *Clinical Gastroenterology* (3d. edition 1983).

Among the chronic disorders of the upper gastrointestinal tract are those which fall under the general categories of gastritis and peptic ulcer disease. (The upper gastrointestinal tract is generally defined as including the esophagus, the stomach, the duodenum, the jejunum, and ilium.) Gastritis is, by definition, typified by an inflammation of the stomach mucosa. In practice, though, the disorder is manifested by a broad range of poorly defined, and heretofore inadequately treated, symptoms such as indigestion, "heart burn", dyspepsia and excessive eructation. A general discussion of gastritis appears in B. J. Marshall and J. R. Warren, "Unidentified Curved Bacilli in the Stomach of Patients with Gastritis and Peptic Ulceration", *The Lancet*, 1311–1315 (1984), and in R. Greenlaw, et al., "Gastroduodenitis, A Broader Concept of Peptic Ulcer Disease", 25 *Digestive Diseases and Sciences* 660–672 (1980).

Peptic ulcers are lesions of the gastrointestinal tract lining, characterized by loss of tissue due to the action of digestive acids and pepsin. It has been generally held that peptic ulcers are caused either by gastric hypersecretion, or (more often) by decreased resistance of the gastric lining to digestive acids and pepsin. The medical literature is replete with methods for treating ulcers, including modification of the diet, surgical removal of the lesions w and the use of drugs. Such drugs include: antacids, which serve to counteract excess gastric secretions; anticholinergics, which reduce acid secretion; H antagonists, which also block the release of gastric acids; prostaglandins, which increase the resistance of the gastric lining to digestive fluids, and may also inhibit acid secretion; prokinetic agents, which enhance gastrointestinal tract motility; and compositions which form protective barriers over gastric lesions. Prescription and non-prescription drug therapies are generally described in Garnet, "Antacid Products", *Handbook of Non-prescription Drugs*, Chapter 3 (7th edition, 1982). One group of drugs which are thought to be effective due to coating of ulcer sites and forming protective barriers is the bismuth-containing drugs. See, for example, Koo, et al., "Selective Coating of Gastric Ulcers by Tripotassium Dicitrato Bismuthate in the Rat", 82 *Gastroenterology* 864–870 (1982).

Regardless of the particular drug composition used in treating gastrointestinal disorders, such as peptic ulcer disease, the treatment is often imprecise and incomplete. Actual "cures", i.e., successful treatment resulting in total remission of disease, are very often not effected. See, A. J. McLean, et al., "Cyto-protective Agents and Ulcer Relapse", 142 *The Medical Journal of Australia*, Special Supplement 525–528 (1985). Furthermore, many conventional treatments may render subjects hypochlorhydric (i.e., with low levels of hydrochloric acid in the stomach) which may predispose them to other disorders, e.g., gastrointestinal infection, halitosis, and gastric carcinomas.

It has now been discovered that certain methods of treatment, involving the administration of bismuth, are effective for the treatment of infectious upper-gastrointestinal disorders. In particular, as compared to treatment regimens known in the art, these methods cure, or afford lower relapse rates of, gastritis and peptic ulcer disease. These methods also afford other benefits in the treatment and management of subjects having gastrointestinal diseases, such as in not rendering subjects hypochlorhydric.

SUMMARY OF THE INVENTION

The present composition provides methods, for the treatment of a human or lower animal subject having an infectious gastrointestinal disorder, comprising the step of administering to said subject from about 50 milligrams to about 5000 milligrams of bismuth, per day, for from 3 to 56 days. Preferred methods of the present invention comprise administration of bismuth to human or lower animal subjects that have been tested for the presence of infection by pyloric campylobacter or similar organisms, with positive results. A preferred test for such infection is through the detection of urease enzyme in the stomach.

DESCRIPTION OF INVENTION

The methods of the present invention comprise treatment of humans or lower animals, having an infectious gastrointestinal disorder, by administering bismuth. Specific compounds and compositions to be used in the processes and compositions of the present invention must, accordingly, be pharmaceutically-acceptable. As used herein, such a "pharmaceutically-acceptable" component is one which is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse effects (such as toxicity, irritation, or allergic response) commensurate with a reasonable benefit/risk ratio when used in the manner of this invention. The specific "safe and effective amount" will, obviously, vary with such factors as the particular condition that is being treated, the severity of the condition, the duration of the treatment, the physical condition of the patient, the nature of concurrent therapy (if any), and the specific formulations employed in the present invention.

Specifically, the processes of the present invention, for the treatment of a human or lower animal subject having an infectious gastrointestinal disorder, comprise the step of administering to said subject from about 50 milligrams to about 5000 milligrams of bismuth, per day, for from about 3 to about 56 days.

As used herein, "infectious gastrointestinal disorder" encompasses any disease or other disorder of the upper gastrointestinal tract of a human or lower animal which is caused or mediated by Campylobacter-like organisms (herein "CLO"), e.g., *Campylobacter pyloridis*. Such CLO include those described in J. R. Warren and B. J. Marshall, "Unidentified Curved Bacilli on Gastric Epithelium in Active Chronic Gastritis", *The Lancet* 1273–1275 (1983), incorporated by reference herein, and G. Kasper and N. Dickgiesser, "Isolation from Gastric Epithelium of Campylobacter-like Bacteria that are Distinct from 'Campylobacter Pyloridis'", *The Lancet* 111–112 (1985). Such infectious gastrointestinal disorders include, for example: CLO-mediated disorders not manifested by presence of ulcerations in the gastric mucosa (herein "non-ulcerative gastrointestinal disorder"), including chronic or atrophic gastritis, non-ulcer dyspepsia, esophogeal reflux disease and gastric motility disorders; and "peptic ulcer disease", i.e., CLO-mediated gastric duodenal, and jejunal ulcers.

As used herein, "administering" refers to any method which, in sound medical practice, delivers the compounds or compositions used in this invention to the subject to be treated in such a manner so as to be effective in the treatment of the infectious gastrointestinal disorder. Preferably, then, the bismuth is administered orally.

Bismuth:

The processes of this invention involve administration of from about 50 milligrams to about 5000 milligrams of bismuth, per day, for from about 3 to 56 days. (As used herein, the quantity of bismuth is by weight of elemental bismuth. Thus, the actual weight of a bismuth-containing compound will be greater. ) Preferably, from about 500 milligrams to about 1500 milligrams of bismuth are administered, per day. The preferred duration of bismuth administration will vary according to the specific gastrointestinal disorder to be treated in general, though, in methods for treatment of non-ulcerative gastrointestinal disorders, the bismuth is administered for from 3 to 21 days. The bismuth is preferably adminstered, in methods for treatment of peptic ulcer disease, for from 14 to 56 days.

In the processes of this invention, the bismuth is preferably administered as a pharmaceutically-acceptable salt. Such bismuth salts include, for example, bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention. The bismuth useful herein may be administered alone, or in combination with other pharmaceutically-acceptable components, in a bismuth-containing composition. A variety of such compositions containing bismuth salts are commercially-available, including, for example, DeNol, containing tripotassium dicitrato bismuthate (sold by Gist-Brocades N.V.), Noralac, containing bismuth aluminate, alginic acid, and magnesium carbonate (manufactured by North American Pharmaceuticals), Roter bismuth, containing bismuth subnitrate ( sold by Roter Laboratories ), Fensobar Polvo, containing bismuth subcarbonate among other materials (manufactured by USV Pharmaceutical Corporation ), and Pepto-Bismol, containing bismuth subsalicylate (sold by The Procter & Gamble Company).

Optional Components and Methods:

The methods of this invention may incorporate optional steps modifying the methods of treatment of this invention. Such optional steps may also utilize optional components or compositions. Such optional components or compositions must not, however, adversely affect the therapeutic activity of the bismuth used in the present methods. Methods for treatment of gastrointestinal disorders, involving administration of bismuth and antimicrobials, are described in copending application Ser. No. 744,841, Marshall, "Methods and Compositions for the Treatment of Gastrointestinal Disorders", filed Jun. 13, 1985 (incorporated by reference herein).

A preferred method of this invention includes a step for the detection of a CLO infection in the stomach of the human or lower animal subject. The methods for detection useful in such preferred steps of this invention include gram stains of gastric tissues (obtained for example by biopsy), serologic tests to detect the presence of antibodies to the organisms, tests of body fluids to detect the presence of metabolites of the organisms, silver stain tissue sections of gastric tissues, and detection of urease enzyme in the stomach of the subject.

The diagnostic step is preferably performed prior to the step of administering bismuth. Also preferably, the diagnostic step is repeated during the step of administering bismuth, and the step of administering bismuth is terminated after the diagnostic step yields a negative result. Thus, such preferred methods, for the treatment of a human or lower animal subject having an infectious gastrointestinal disorder, comprise the steps of:

a) performing a diagnostic test on said subject for the detection of a CLO infection of said subject; and, upon obtaining a positive result from said diagnostic test, b) administering to said subject from about 50 milligrams to about 5000 milligrams of bismuth, per day, for a period of time ending when said subject is tested with said diagnostic test and a negative result is obtained.

One preferred method of detection, useful in a preferred process of this invention, is the detection of urease enzyme (urea amidohydrolase) in the stomach of the human or lower animal having a gastrointestinal disorder. Such a detection step may include, for example, obtaining a sample of gastric fluid (e.g., from vomitus) or of gastric mucosa (e.g., by biopsy) and analyzing the material for the presence of urease enzyme. One such method for the diagnosis of gastrointestinal disorder is described in copending application Ser. No. 744,840, Marshall, "Compositions and Methods For The Diagnosis of Gastrointestinal Disorders", filed Jun. 13, 1985. Such methods involve obtaining a sample of gastric mucosa and placing said sample into a composition which comprises:

a) urea, at a concentration of from about 10 to about 40 grams per liter;

b) a bactericide, at a concentration of from about 1 to about 5 grams per liter;

c) an indicator having a $pK_a$ of from about 6.5 to about 8.5, at an effective concentration; and d) water;

wherein said composition has a pH of from about 5.0 to about 6.5 and said pH is at least one pH unit lower than the $pK_a$ of said indicator. Preferably, the composition contains a gelling agent, such as a non-nutritive agar, at a concentration of from about 5 to about 50 grams per liter. Typically the indicator is present at a concentration of from about 20 to about 100 milligrams per liter. (As used herein, all concentrations are by weight of component per volume of total composition.) A change in the color of the composition indicates the presence of urease enzyme, and the presence of a gastrointestinal disorder.

The following non-limiting examples illustrate the compositions, processes, and uses of the present invention.

EXAMPLE I

A human subject, suffering from atrophic gastritis, is treated by a method of the present invention. Specifically, the subject is endoscoped and a biopsy taken of the gastric mucosa of the subject. Analysis of the biopsy sample shows inflammation of the mucosa, and depletion of the protective mucous layer. Histological examination of the sample also reveals the presence of *Campylobacter pyloridis*. The subject is then treated, according to the present invention, by administering a composition containing bismuth subsalicylate, sold by The Procter & Gamble Company under the name "Pepto-Bismol". The composition, in liquid form, is administered four times daily in equal doses of 30 milliliters (for a total of approximately 1200 milligrams of bismuth administered per day) for 21 days. Thereafter, the subject is endoscoped and biopsied again, finding essentially normal, healed gastric mucosa. Histological examination of the gastric material sample does not reveal any bacterial infection. The subject remains asymptomatic, and another biopsy performed five months later reveals normal gastric mucosa.

In the above example, tripotassium dicitrato bismuthate, bismuth tartrate, bismuth citrate, and bismuth subnitrate are substituted, respectively, for bismuth subsalicylate, with substantially similar results.

EXAMPLE II

A human subject, suffering from peptic ulcer disease, is treated by a method of this invention. Specifically, a biopsy of gastric mucosa is taken from the stomach of the subject. The sample is then placed in 0.5 milliliters of an aqueous gel having the following composition:

| Component | Quantity (grams) | Final Concentration |
|---|---|---|
| urea | 3.000 | 30 g/l |
| phenol red* | 0.008 | 80 mg/l |
| methyl hydroxy benzoate | 0.200 | 2 g/l |
| bacteriological agar | 1.500 | 15 g/l |
| citric acid | 0.040 | 400 mg/l |
| sodium phosphate | 0.080 | 800 mg/l |

*phenol sulfonphthalein indicator, having $pK_a = 7.9$, exhibiting a yellow color in undissociated state (below pH 6.4) and red color in dissociated state (above pH 8.2)

(The components, except for urea, are dissolved in 100 milliliters of water, heated to approximately 65° C., and stirred until the solution is clear. The composition is allowed to cool to below approximately 45° C., and the urea is added. Upon cooling to ambient temperature, a gel is formed, having a pH of 6.0 and a deep yellow color.) After the biopsy sample is inserted into the composition, the composition color changes from deep yellow to red over a period of fifteen minutes, indicating the presence of urease in the biopsy sample and presence of CLO in the stomach of the subject. The subject is then treated by administering 700 milligrams of bismuth, as bismuth subsalicylate, per day, for 35 days. Thereafter, the subject is endoscoped, revealing normal gastric mucosa and healing of the peptic ulcer crater, and a biopsy sample is obtained. The sample is then inserted into 0.5 milliliters of a test composition comprised as above, and the color of the composition remains unchanged after 24 hours, indicating lack of CLO infection.

What is claimed is:

1. A method, for the treatment of a human or lower animal subject having an infectious gastrointestinal disorder caused or mediated by *Campylobacter pyloridis*, by combating said *Campylobacter pyloridis* infection in said subject, comprising the step of orally administering to said subject from about 50 milligrams to about 5000 milligrams of bismuth, per day, for from 3 to 56 days, wherein said bismuth is selected from the group consisting of bismuth aluminate, bismuth subcarbonate, bismuth citrate, bismuth subgalate, bismuth subnitrate, bismuth tartrate, bismuth subsalicylate, and mixtures thereof.

2. A method, according to claim 1, wherein said bismuth is administered at a level of from about 500 to about 1500 milligrams, per day.

3. A method, according to claim 1, for the treatment of a human or lower animal subject having a non-ulcerative gastrointestinal disorder, wherein said bismuth is administered for from 3 to 21 days.

4. A method, according to claim 1, for the treatment of a human or lower animal subject having peptic ulcer disease, wherein said bismuth is administered for from 14 to 56 days.

5. A method, according to claim 3, wherein said bismuth is bismuth subsalicylate.

6. A method, according to claim 4, wherein said bismuth is bismuth subsalicylate.

7. A method, for the treatment of a human or lower animal subject having an infectious gastrointestinal disorder caused or mediated by *Campylobacter pyloridis*, by combating said *Campylobacter pyloridis* infection in said subject, comprising the steps of:

(a) performing a diagnostic test on said subject, for the detection of a *Campylobacter pyloridis* infection of said subject; and, upon obtaining a positive result from said diagnostic test, (b) orally administering to said subject from about 50 milligrams to about 5000 milligrams of bismuth, per day, for from 3 to 56 days, wherein said bismuth is selected from the group consisting of bismuth aluminate, bismuth subcarbonate, bismuth citrate, bismuth subgalate, bismuth subnitrate, bismuth tartrate, bismuth subsalicylate, and mixtures thereof.

8. A method, according to claim 7, wherein said bismuth is administered for a period of time ending when said subject is tested with said diagnostic test and a negative result is obtained.

9. A method for treating peptic ulcer disease caused or mediated by *Campylobacter pyloridis* by combating said *Campylobacter pyloridis* infection in a human or lower animal subject comprising the step of orally administering to said subject from about 50 milligrams to about 5,000 milligrams of bismuth, per day, for from 3 to 56 days.

10. A method, according to claim 9, wherein said bismuth is selected from the group consisting of bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof.

11. A method, according to claim 10, wherein said bismuth is tripotassium dicitrato bismuthate.

12. A method, according to claim 10, wherein said bismuth is bismuth subsalicylate.

13. A method for treating non-ulcerative gastrointestinal disorder caused or mediated by *Campylobacter pyloridis* by combating said *Campylobacter pyloridis* infection in a human or lower animal subject comprising the step of orally administering to said subject from about 50 milligrams to about 5000 milligrams of bismuth, per day, for from 3 to 56 days, wherein said bismuth is selected from the group consisting of bismuth aluminate, bismuth subcarbonate, bismuth citrate, bismuth subgalate, bismuth subnitrate, bismuth tartrate, bismuth subsalicylate, and mixtures thereof.

14. A method, according to claim 13, wherein said bismuth is bismuth subsalicylate.

15. A method for treating non-ulcerative dyspepsia caused or mediated by *Campylobacter pyloridis* by combating said *Campylobacter pyloridis* infection in a human or lower animal subject comprising the step of orally administering to said subject from about 50 milligrams to about 5000 milligrams of bismuth, per day, for from 3 to 56 days, wherein said bismuth is selected from the group consisting of bismuth aluminate, bismuth subcarbonate, bismuth citrate, bismuth subgalate, bismuth subnitrate, bismuth tartrate, bismuth subsalicylate, and mixtures thereof.

16. A method, according to claim 15, wherein said bismuth is bismuth subsalicylate.

17. A method for treating gastritis caused or mediated by *Campylobacter pyloridis* by combating said *Campylobacter pyloridis* infection in a human or lower animal subject comprising the step of orally administering to said subject from about 50 milligrams to about 5000 milligrams of bismuth, per day, for from 3 to 56 days, wherein said bismuth is selected from the group consisting of bismuth aluminate, bismuth subcarbonate, bismuth citrate, bismuth subgalate, bismuth subnitrate, bismuth tartrate, bismuth subsalicylate, and mixtures thereof.

18. A method for treating gastritis caused or mediated by *Campylobacter pyloridis* by combating said *Campylobacter pyloridis* infection in a human or lower animal subject comprising the step of orally administering to said subject from about 50 milligrams to about 5,000 milligrams of bismuth, per day, for from 3 to 21 days, wherein said bismuth is bismuth subsalicylate.

19. A method for treating duodenal ulcers caused or mediated by *Campylobacter pyloridis* by combating said *Campylobacter pyloridis* infection in a human or lower animal subject comprising the step of orally administering to said subject from about 50 milligrams to about 5,000 milligrams of bismuth, per day, for from 14 to 56 days, wherein said bismuth is bismuth subsalicylate.

20. A method for treating duodenal ulcers caused or mediated by *Campylobacter pyloridis* by combating said *Campylobacter pyloridis* infection in a human or lower animal subject comprising the step of orally administering to said subject from about 50 milligrams to about 5,000 milligrams of bismuth, per day, for from 14 to 56 days, wherein said bismuth is tripotassium dicitrato bismuthate.

21. A method for treating gastric ulcers caused or mediated by *Campylobacter pyloridis* by combating said *Campylobacter pyloridis* infection in a human or lower animal subject comprising the step of orally administering to said subject from about 50 milligrams to about 5,000 milligrams of bismuth, per day, for from 14 to 56 days, wherein said bismuth is tripotassium dicitrato bismuthate.

22. A method of treating patients suffering from non-ulcer dyspepsia associated with *Campylobacter pyloridis* infection, said method comprising administering to said patients a composition comprising pharmaceutically acceptable bismuth salt in an amount effective to clear said patients of dyspeptic symptoms.

* * * * *